(12) United States Patent
Radwin et al.

(10) Patent No.: US 9,566,004 B1
(45) Date of Patent: Feb. 14, 2017

(54) APPARATUS, METHOD AND SYSTEM FOR MEASURING REPETITIVE MOTION ACTIVITY

(71) Applicants: Robert G. Radwin, Waunakee, WI (US); Yu Hen Hu, Madison, WI (US); Chia-Hsiung Chen, Madison, WI (US); Thomas Y Yen, Madison, WI (US)

(72) Inventors: Robert G. Radwin, Waunakee, WI (US); Yu Hen Hu, Madison, WI (US); Chia-Hsiung Chen, Madison, WI (US); Thomas Y Yen, Madison, WI (US)

(73) Assignee: KINEVID, LLC., Waunakee, WI (US)

( * ) Notice: Subject to any disclaimer, the term of this patent is extended or adjusted under 35 U.S.C. 154(b) by 272 days.

(21) Appl. No.: 13/681,538

(22) Filed: Nov. 20, 2012

Related U.S. Application Data (60) Provisional application No. 61/562,628, filed on Nov. 22, 2011.

(51) Int. Cl.
*A61B 5/00* (2006.01)

(52) U.S. Cl.
CPC .................. *A61B 5/0002* (2013.01)

(58) Field of Classification Search
CPC .............................. A61B 5/112; A61B 5/1128
USPC .......................................................... 600/595
See application file for complete search history.

(56) References Cited

U.S. PATENT DOCUMENTS

| | | | |
|---|---|---|---|
| 7,330,566 B2 * | 2/2008 | Cutler | 382/103 |
| 2006/0204045 A1 * | 9/2006 | Antonucci | 382/107 |

OTHER PUBLICATIONS

Mark Wilson, "Testing Project Natal: We Touched the Intangible", Jun. 3, 2009. http://gizmodo.com/5277954/testing-project-natal-we-touched-the-intangible/.*
Mike Schramm, "Kinect: The company behind the tech explains how it works", Jun 19, 2010. http://www.joystiq.com/2010/06/19/kinect-how-it-works-from-the-company-behind-the-tech/.*
Alex Pham, "E3:Microsoft shows off gesture control technology for Xbox 360", Jun. 1, 2009. http://latimesblogs.latimes.com/technology/2009/06/microsofte3.html.*
Stephen Totilo, Natal Recognizes 31 Body Parts, Uses Tenth of Xbox 360 "Computing Resources", Jan. 1, 2010. http://kotaku.com/5442775/natal-recognizes-31-body-parts-uses-tenth-of-xbox-360-computing-resources.*

(Continued)

*Primary Examiner* — Adam J Eiseman
*Assistant Examiner* — Yasmeen S Warsi
(74) *Attorney, Agent, or Firm* — Casimir Jones SC (57) ABSTRACT

Provided herein are systems and methods that use a video content analysis algorithm to measure and quantify repetitive motion activity of a designated body part, including velocity, acceleration, frequency, and duty cycle, without applying sensors or other instrumentation to the body, for the purpose of preventing repetitive motion injuries. In some embodiments, the video-based direct exposure assessment system uses marker-less video and a video content analysis algorithm. The video content analysis algorithm is able to recognize and identify the pattern of repetitive motion, through a process known as cyclic motion analysis. Determination of the cycle pattern provides parameters for determining a body part's activity level, and thereby allows determination of the body part's activity level.

16 Claims, 6 Drawing Sheets is an exemplary embodiment of a repetitive motion analysis system implemented as a separate video camera and software executed on a laptop computer.

(56) References Cited

OTHER PUBLICATIONS

Drinkaus, Phillip, Sesek, Richard, Bloswick, Donald S., "Job Level Risk Assessment Using Task Level ACGIH Hand Activity Level TLV Scores: A Pilot Study", Internationl Journal of Occupational Safety and Ergonomics (JOSE) 2005, vol. 11, No. 3, 263-281.*

Chen, Chia-Hsiung, et al. "Automated video exposure assessment of repetitive hand activity level for a load transfer task." Human Factors: The Journal of the Human Factors and Ergonomics Society (2013), 55(2): 298-308.

* cited by examiner

FIG. 1 is an exemplary flow diagram depicting an embodiment of the data-analyzing algorithm.

FIG. 2 is an exemplary flow diagram depicting an embodiment of the algorithm.

FIG. 3 is an exemplary flow diagram depicting an embodiment of the data-analyzing algorithm.

FIG. 4 is an exemplary embodiment of a system and apparatus for applying video analysis to repetitive motion activities.

FIG. 5 is an exemplary embodiment of a system and apparatus for applying video analysis to repetitive motion activities.

FIG. 6 is an exemplary embodiment of a system and apparatus for applying video analysis to repetitive motion activities.

FIG. 7 is an exemplary embodiment of a repetitive motion analysis system implemented as a separate video camera and software executed on a laptop computer.

FIG. 8 is an exemplary embodiment of a repetitive motion analysis system implemented as a hand-held camera enabled device.

APPARATUS, METHOD AND SYSTEM FOR MEASURING REPETITIVE MOTION ACTIVITY

This application claims priority to U.S. Provisional Patent Application Ser. No. 61/562,628, filed Nov. 22, 2011, the disclosure of which is herein incorporated by reference in its entirety.

FIELD

Provided herein is a device, method and system that measures and quantifies repetitive motion activity of a designated body part of a subject, including velocity, acceleration, frequency, and duty cycle, without applying sensors or other instrumentation to the body, for the purpose of preventing muscle fatigue and repetitive motion injuries.

BACKGROUND

Musculoskeletal injuries account for about 3 million occupational injuries annually in the United States. Shane Shapiro, *Worker's Compensation Claims Related to Musculoskeletal Injuries*, 57 NORTHEAST FLORIDA MEDICINE 41, 43 (2006). Musculoskeletal injuries are common in repetitive physically intensive work. Repetitive motion injuries (e.g. sprains, strains, tendinitis, tendosynovitis, and carpal tunnel syndrome) are a major concern today. Sprains, strains, tendinitis and carpal tunnel syndrome accounted for 41 percent of the injuries and illnesses resulting in days away from work in 2010. Bureau of Labor Statistics, U.S. Dep't of Labor (2011). Over 30,000 work-related repetitive motion injuries are reported annually in private industry in the United States. Bureau of Labor Statistics, U.S. Dep't of Labor (2008). Repetitive motion injuries have the highest median recovery time of all workplace reported injuries and illnesses, with a median twenty-four work days lost for recovery. Bureau of Labor Statistics, U.S. Dep't of Labor (2011). One of the top ten causes of disabling workplace injuries and illness, repetitive motion injuries account for over $1.8 billion in annual workers compensation costs. Liberty Mutual 2010 Annual Workplace Safety Index. Upper extremity injuries are prevalent in repetitive hand intensive work. See Z. J. Fan et al., *Quantitative Exposure-response Relations between Physical Workload and Prevalence of Lateral Epicondylitis in a Working Population*, 52 AM. J. INDUS. MED. 479-90 (2009); B. Silverstein et al., *The Natural Course of Carpal Tunnel Syndrome in a Working Population*, 36 SCAND. J. WORK ENVTL. HEALTH. 384-93 (2010).

Yet there is currently no practical way to objectively and efficiently measure repetitive motion exposure. See Z. J. Fan et al., supra; A. Garg & J. Kapellusch, *Consortium Pooled Data Job Physical Exposure Assessment*, 17$^{TH}$ WORLD CONGRESS IN ERGONOMICS, Beijing, China, (2009); K. T. Hegmann et al., *Prospective Cohort Study of Upper Extremity MSDs Among 17 Diverse Employers*, 17$^{TH}$ WORLD CONGRESS IN ERGONOMICS, Beijing, China (2009); and B. Silverstein et al., supra. For example, for measurements of upper limb kinematics, current methods involve either direct measurements using instruments attached to a worker's hands or arms, or indirect observations. A commonly employed observational method for quantifying the degree of repetition in upper extremities is the Hand Activity Level (HAL) scale, which is based on the ten point visual-analog scale. W. A. Latko et al., *Development and evaluation of an observational method for assessing repetition in hand tasks*, 58 AM. INDUS. HYGIENE ASS'N J. 278-85 (1997). HAL is a factor used to ascertain the threshold limit value for repetitive manual tasks. AM. CONF. OF GOVERNMENTAL INDUS. HYGIENISTS, HAND ACTIVITY LEVEL TLVS® AND BEIS® BASED ON THE DOCUMENTATION OF THE THRESHOLD LIMIT VALUES FOR CHEMICAL SUBSTANCES AND PHYSICAL AGENTS & BIOLOGICAL EXPOSURE INDICES, 196-98 (2009). The HAL scale ranges from 0 to 10, and quantifies repetitive motion ranging from idle hand activity (0) to rapid steady motion with difficulty keeping up (10). Under current methods, a trained observer calculates HAL using either subjective estimation or objective measurements of frequency and duty cycle from a stopwatch time study or a manual frame-by-frame video analysis.

HAL is based on duty cycle and exertion frequency. For many tasks, these are associated with hand and arm movements and static or dynamic exertions. The frequency is the rate of repetition in cycles per second or Hz. The duty cycle is the percent ratio of hand exertion time to the total cycle time of the activity (i.e. exertion time/cycle time). Consequently a 100 percent duty cycle refers to repetitive work where force is exerted for the entire time and a 50 percent duty cycle occurs when force is exerted half of the time.

Current methods of measuring and calculating limb kinematics have been mostly limited to research studies and are highly impractical for routine occupational health and safety practice. The conventional approaches for rating repetitive limb activity based on observable characteristics of manual work are inaccurate, cumbersome or impractical for routine work evaluation and have been limited primarily to research laboratories. Compared to instruments, observation is noninvasive but lacks precision and accuracy, is not suitable for long observation periods, and requires considerable analyst time. B. D. Lowe, *Accuracy and Validity of Observational Estimates of Shoulder and Elbow Posture*, 35 APPLIED ERGONOMICS 159-71 (2004). Alternatively, attaching sensors on working limbs is time consuming, and sensors may interfere with normal working operations. Thomas Y. Yen & Robert G. Radwin, *Comparison Between Using Spectral Analysis of Electrogoniometer Data and Observational Analysis to Quantify Repetitive Motion and Ergonomic Changes in Cyclical Industrial Work.* 43 ERGONOMICS 106-32 (2000). Not only is existing instrumentation use resource intensive, but the required technical knowledge often makes this approach inaccessible to general industry.

SUMMARY OF THE INVENTION

Conventional methods of evaluating repetitive motion activities in work environments, using either a trained observer on or off site, or manual off site video analysis, are often considered inaccurate, cumbersome or impractical for routine work assessment. Provided herein is technology that provides the option for automatic, unobtrusive, and objective exposure assessment to prevent and control exposure to repetitive motions related to muscle fatigue and injuries in the workplace. In particular, a noninvasive real-time video content analysis framework is provided that can automatically measure limb activity levels using, for example, conventional digital videos focused on the work activity. Provided herein is an automatic video analysis of repetitive hand activity for occupational health and safety assessment.

Video-based direct exposure assessment provides a new mechanism for preventing and controlling exposure to repetitive motion. A direct video assessment method that uses, for example, digital video processing to automatically measure repetitive motion exposure has several advantages over traditional repetitive motion exposure assessment methods. The use of marker-less video is unobtrusive and does not require attaching sensors to a worker's body, which often interferes with the job and possibly movement patterns and exertions. The marker-less video approach is made practical by relaxing the need for the high precision normally important for spatiotemporal motion tracking of joints and body linkages, but which is not necessary for limb activity levels, by emphasizing temporal patterns and by adopting a semi-automatic approach whereby the analyst uses discretion to interactively select a region of interest associated with the repetitive task, such as a hand or arm to track relative to a stationary region, rather than imposing an a priori model of the tracked activity. Consequently the analysis complexity is greatly reduced and may be more tolerable of the numerous variations encountered in field video recordings of occupational tasks. The direct video assessment device is capable of performing the analysis in real-time. The direct video assessment method and system requires minimal human intervention and discretion. Consequently the subjectivity issue is eliminated since, for example, the analysis is determinate for a given video segment. Furthermore such an application may be ported to programmable, camera-enabled mobile devices. When embodied in a programmable, camera-enabled computer, a video-based direct exposure assessment device is contemplated to lower the instrumentation barrier and increase the accuracy of assessment, thereby making analysis of repetitive motion related occupational hazards more accessible to general industry.

A video-based direct exposure assessment system that uses marker-less video is simple to use and requires only a minimal level of training, thereby reducing personnel cost as well. The combination of reduced instrumentation cost and reduced personnel cost allows broader study, and helps reduce the workplace risks of muscle fatigue and of repetitive motion injuries.

In some embodiments, provided herein is a device comprising: an input component; a processor component that is configured to identify and track the repetitive motion of at least one region of interest (ROI); and an output component. In some embodiments, the input component is a user input component with which a user selects, from an image of a subject's body and a background, a single region, or multiple regions, of interest (ROI) on the image of the subject's body. In some embodiments, the input component further includes a component with which the user selects a stationary region (ROS) from the background. In some embodiments a single or multiple ROI(s) or ROS(s) are automatically selected. In some embodiments, the processor component is further configured to perform cyclic motion analysis on the ROI, and to quantify spatiotemporal characteristics of the ROI, including its frequency, duty cycle, and activity level. In some embodiments, the device is further configured to track motion of the video ROI without use or application of any markers on the subject. In some embodiments, the input component includes a sensor component. In some embodiments, the sensor component is an image capture component that relays information to a processor. In some embodiments, the sensor component is configured to communicate with the processor. In some embodiments the image capture component is a camera. In some embodiments the image capture component is a digital video recorder. In some embodiments, the user input component is configured such that a user interacts with the component to select one or more video ROI(s), corresponding to one or more region(s) of interest on one or more body part(s) of a subject. In some embodiments, the user input component is further configured such that the user selects a stationary region (ROS) from the background. In some embodiments the device further comprises an interface by which a user may directly input information, view and interact with overlaid images on a video display and review the results. In some embodiments the system is initialized by selection of a region of interest (ROI) and a stationary region (ROS). In some embodiments the system is initialized by selection of multiple regions of interest and the stationary region. In some embodiments the user performs the initialization of the system by selection of the region of interest (ROI) and the stationary region. In some embodiments the user initializes the system by selecting multiple regions of interest and the stationary region. In some embodiments, the processor component is configured to track motion of the video ROI(s) without use or application of any markers on said subject. In some embodiments, the processor component is configured to identify repetitive motion of the ROI(s). In some embodiments, the processor component is configured to quantify frequency and duty cycle of the selected ROI(s), and to calculate an activity level of the ROI(s). In some embodiments, the processor component is further configured to quantify movement velocity and acceleration of the selected video ROI(s). In some embodiments, the output component is configured to generate a report of the activity level of the ROI. In some embodiments multiple ROIs may be selected. In some embodiments the ROIs are on images of multiple parts of a body, and the device provides a measure of activity level for each body part. In some embodiments, the device further comprises a camera motion compensation component. In some embodiments, the camera motion compensation component provides an estimate for the camera's motion. The estimated camera motion information can be used to correct the body part displacement quantity and provide better estimates of the activity level value. In some embodiments, the processor component is further configured to compensate for camera motion. In some embodiments, the camera motion compensation component comprises: a gyroscope attached to the camera, and an algorithm that extracts orientation and motion information of the camera from the gyroscope. In some embodiments, the camera motion compensation component comprises an accelerometer attached to the camera and an algorithm to extract orientation and motion information of the camera from the accelerometer. In some embodiments, the device further comprises a recording component that records spatiotemporal characteristics representing a sub-image. In some embodiments, the device further comprises a storage component that stores spatiotemporal characteristics in a history array, or journal, with respect to time. In some embodiments, the device is further configured such that each pixel intensity representing a sub-image is recorded and stored in an intensity history with respect to time. In some embodiments the processor component is further configured such that it further comprises an algorithm that operates by identifying and tracing a pixel pattern that best resembles the selected ROI as it changes location in successive video frames. In some embodiments, the velocity of the pixel pattern, relative to a stationary pixel region, is used to estimate the rate of repetition and pauses needed to calculate the activity level. In some embodiments, the processor component is further configured such that the assessment of temporal properties of cyclic movement is based on pixel-based spatiotemporal properties of a tracked ROI relative to a stationary landmark. In some embodiments the device further comprises: a motion-tracking component that performs body part tracking in real time; an algorithm that identifies and reports a new location of the region under investigation as the video stream advances in time; and an algorithm that processes the new location information to assess the spatiotemporal characteristics of movement between two or more image frames. In some embodiments a camera distance from the observed body part to the camera (camera distance) is fixed and is used to calibrate velocity and acceleration. In some embodiments the camera distance is variable and measured using an optical or video continuous distance-measuring component. In some embodiments the ROI is on the image of a limb of a body. In some embodiments quantification of the spatiotemporal characteristics provides a quantitative measure of an activity level of the limb. In some embodiments, the measured region of interest is on an image of an arm or a hand of a human body, and the quantified measure provided is the hand activity level (HAL). In some embodiments the ROI is on an image of a body part of an animal. In some embodiments the ROI is on an image of a machine part. In some embodiments the device is embodied in a computer. "Computer" as used herein refers to any computing device, including any programmable computing device. In some embodiments, the device is embodied in a programmable, camera-enabled computer. In some embodiments, the device is embodied in a self-contained direct reading exposure assessment measurement machine that quantifies repetitive motion. In some embodiments the device is portable. In some embodiments the device is small enough to be carried comfortably and used by an individual. In some embodiments, the device weighs no more than six kilograms in its full embodiment. In some embodiments, the device weighs more than one gram and less than six kilograms. Because the current range in size of portable computers extends from smart phones less than 100 gm to lap top computers that weigh up to six kilograms, it is envisioned that the weight of this device when embodied in a portable computer will fall within the range of existing portable computers. However, in some embodiments the weight may be less than 100 gm, as portable computers continue to diminish in size. There may be some embodiments where the weight of the device embodied in a portable computer is less than 10 gm. In some embodiments the device is embodied in a hand-held computer. In some embodiments the hand-held computer is camera enabled. In some embodiments the computer resides in a smart cellular phone. In some embodiments the device is embodied in a computer that has an interactive input component. In some embodiments the computer has a touch-screen. In some embodiments the computer has a visual display. In some embodiments the computer's visual display is interactive. In some embodiments, the device further comprises a component for mounting the device on a weight bearing structure. In some embodiments the device comprises a component for mounting used at the location where a subject incurs repetitive motion. In some embodiments, said location is an industrial setting. In some embodiments, said location is an occupational setting. In some embodiments, said location is a workplace. In some embodiments, said location is a site where repetitive motion activities are performed. In some embodiments the device has a component that provides feedback to permit a user to quantify measurements. In some embodiments, the device has a component that provides feedback to permit a user to prevent repetitive motion injuries. In some embodiments the device has a component that provides feedback to permit a user to prevent muscle fatigue. In some embodiments the device is configured to indicate whether a repetitive motion is likely to cause injury. In some embodiments the device is configured to indicate whether muscle fatigue is likely to cause injury. In some embodiments, the device further comprises a component that generates a report. In some embodiments, the report includes a graphic output of the activity level relative to load. In some embodiments, the report includes a graphic output of the activity level relative to time. In some embodiments, the report includes a graphic output of risk to the subject of incurring a repetitive motion injury, relative to load, based on the calculated activity level. In some embodiments, the report includes a calculation of the risk to the subject of incurring repetitive motion injuries based on the calculated activity level, given a calculated or specified load. In some embodiments, the report includes a warning signal if the activity level exceeds a threshold value beyond which repetitive motion injury is likely. In some embodiments, the report includes a textual description of possible precautions to decrease the risk of repetitive motion injury. In some embodiments, the report includes a graphic display of possible precautions to decrease the risk of repetitive motion injury. In some embodiments, the processor component of the device is configured to monitor the motion of the ROI. In some embodiments, the processor component is further configured to perform the cyclic motion analysis on the ROI. In some embodiments, the device automatically detects and records when the limb is load bearing. In some embodiments, the processor is further configured to calculate the duty cycle based on the percentage of time that the limb is load bearing over cycle time. In some embodiments, the processor component of the device further performs a method to predict and update ROI location for reliable ROI tracking.

In some embodiments provided herein is a device comprising a processor configured with a marker-less algorithm that uses video from at least one camera to track motion with sufficient accuracy to evaluate injury risk to a body or a subject under field conditions. In some embodiments one or more cameras may receive light in any combination of the visual spectrum, the infrared spectrum or the ultraviolet spectrum. In some embodiments said processor is configured to quantify a repetitive motion of a video region of interest (ROI) that the user selects from an image of a part of a body. In some embodiments, the processor is configured to select the ROI. In some embodiments said processor is configured to quantify repetitive motion from multiple regions of interest. In some embodiments the spatiotemporal properties of a selected video ROI are measured using marker-less motion tracking that does not require any markers or external sensors to be worn by the body or subject. In some embodiments the video ROI is on an image of a limb of the body. In some embodiments the video ROI is on an image of a limb of an animal. In some embodiments the video ROI is on an image of a machine part. In some embodiments the video ROI is on an image of an arm or a hand of a human body, and the processor is configured to provide output in the form of an activity level (HAL) of the arm or hand. In some embodiments an interface component provides output of a measure of the activity level of a body part. In some embodiments the device provides output information regarding the activity levels of multiple body parts. In some embodiments the component by which the device provides an interface with the user is configured for the user to directly input information, view and interact with overlaid images on a video display and review the results. In some embodiments the device is small enough to be carried comfortably and used by an individual, such as from five grams to six kilograms in weight. In some embodiments the device is embodied in a hand-held computer. In some embodiments said hand-held computer is camera-enabled.

In some embodiments the device resides in a smart cellular phone. In some embodiments the device resides in a computer with an interactive input component. In some embodiments said device is embodied in a computer with a touchscreen. In some embodiments said device is embodied in a computer with an interactive visual display. In some embodiments the device comprises a component for mounting on a weight-bearing structure near a location where a subject incurs repetitive motion. In some embodiments said location is an occupational setting. In some embodiments the location is an industrial setting. In some embodiments the location is a workplace. In some embodiments the device has a component that provides feedback to permit a user to prevent repetitive motion injuries. In some embodiments, the device is configured for efficient and practical use by practitioners in a field.

In some embodiments provided herein is a device comprising a processor that is configured to perform the steps of an algorithm that further comprises: an algorithm that recognizes and identifies the pattern of repetitive motion of a part of a body, through a process known as cyclic motion analysis, by tracking the motion of a selected region of interest on an image of that body part relative to a selected stationary region from the background of the image; and calculates the activity level of that body part. In some embodiments a user initializes a cross-correlation based tracking algorithm by selecting a region, or multiple regions, of interest (ROI) in order to identify the focal area; and the tracking algorithm tracks the ROI motion trajectory over successive video frames. In some embodiments, the ROIs are polygonal. In some embodiments the motion tracking provides positive and negative values. In some embodiments, the processor is further configured to compute a motion history curve with positive and negative values that are obtained from motion tracking, wherein the frame numbers that contain the boundary-crossing are determined, and wherein a cycle is defined as the period of time between two positive-to-negative, or two negative-to-positive, boundary-crossing points. In some embodiments, the processor is further configured to calculate a velocity $(v_x, v_y)$ vector and an acceleration $(a_x, a_y)$ vector for the center of the ROI at each time stamp as follows:

$$v_{p,i} = (p_{i+1} - p_{i-1})/2\Delta$$

$$a_{p,i} = (p_{i+1} - 2 \times p_i + p_{i-1})/\Delta^2$$

wherein $p \in \{x,y\}$, $i \in \{2, 3, \ldots\}$ and $\Delta = 1/30$ second, which is the sample rate of the video. The video velocity and acceleration magnitude are determined by:

$$v_{xy,video} = \sqrt{(v_x)^2 + (v_y)^2}$$

$$a_{xy,video} = \sqrt{(a_x)^2 + (a_y)^2}$$

In some embodiments, the boundary-crossing detection is performed on a filtered curve, such as a high frequency removed direction curve. In some embodiments the algorithm identifies cycles by detecting crossings of a gating patch, and a cycle is defined as the period of time between two right-to-left, or left-to-right, gating patch crossings. In some embodiments a cyclic motion analysis algorithm estimates the cycle time based on boundary-crossings of the ROI relative to a stationary gating region. In some embodiments the algorithm computes a duty cycle D as the fraction of cycle time that the ROI's moving velocity was greater than a threshold; and computes activity level of the body part as a function of the cycle time and the duty cycle. In some embodiments the algorithm further comprises one or more of the following operations based on one or more of the following definitions: Let $r_i$ be a vector of intensity values of all pixels within the ROI at the $i^{th}$ frame, and $r_{i+1}(w)$ be a candidate ROI at the $(i+1)^{th}$ frame with a displacement of $w \in \Omega$ in a pre-specified search area; and let $\Omega$ be determined based on the prior knowledge of the velocity of arm movement (pixels/frame). In some embodiments, the cross-correlation between $r_i$ and $r_i+1(w)$ is defined as the angle between these two vectors ($\|r_i\|$ is the magnitude of the vector $r_i$, $r_i^T$ is the transpose of $r_i$):

$$R(w) = r_i^T r_{i+1}(w)/(\|r_i\| \cdot \|r_{i+1}(w)\|)$$

In some embodiments, the displacement $w^* = \arg\max_W R(w)$ determines the updated position of the ROI at the $(i+1)^{th}$ frame, $r_{i+1} = r_{i+1}(w^*)$. The sequence of $w^*$ is recorded as the velocity of the motion between these two frames, and the new position of the ROI yields the motion trajectory at the $(i+1)^{th}$ frame. In some embodiments, given a list of P frame numbers fr=$\{fr_0, fr_1, fr_2, \ldots, fr_{P-1}\}$ in which crossing occurred, the number of cycles C is defined as: C=(# of elements in fr)$-1=P-1$ In some embodiments, the duty cycle D is defined as the ratio of motion time with respect to total observation time. In some embodiments, the duty cycle D is defined as the ratio of number of active frames to the total number of frames. In some embodiments, active frames are defined as those frames that have motion speed larger than or equal to a predefined threshold. In some embodiments, the number of active frames is denoted as $fr_{active}$, and the total number of frames within the entire observation is denoted as $fr_{total}$. In some embodiments, duty cycle D is determined by the equation, D=($fr_{active}/fr_{total}$)×100%.

In some embodiments, the frequency of the body part's motion f is determined by the time the body part is moving, as if the task is done at 100% duty cycle. In some embodiments, the frequency f is defined as inverse of average active cycle time. In some embodiments, f is represented as a function of number of active frames:

$$f = \frac{1}{(fr_{active}/C)/(\text{frame rate})}$$

In some embodiments, an exertion time is defined as the time during which an exertion is occurring, and exertion frames are defined as those frames captured during the exertion time. In some embodiments, the duty cycle D is defined as the ratio of the exertion time with respect to total cycle time. In some embodiments, the duty cycle D is defined as the ratio of the number of exertion frames to the total number of frames. In some embodiments, an exertion is defined as a simple movement of a body part or item being tracked as the ROI. In some embodiments, an exertion is defined as an action associated with a muscle contraction or group of muscle contractions. In some embodiments, the number of exertion frames is denoted as $fr_{exert}$, and the total number of frames within the entire observation is denoted as $fr_{total}$. In some embodiments, duty cycle D is determined by D=($fr_{exert}/fr_{total}$)×100%. In some embodiments, the frequency of the body part's motion f is determined by the time the body part is moving, as if the task is done at 100% duty cycle. In some embodiments, the frequency f is defined as inverse of average active cycle time. In some embodiments, the active cycle time is measured in turns of number of active frames, wherein the active frames are defined as those frames that have motion speed larger than or equal to a predefined threshold. In some embodiments, the number of active frames is denoted as fr$_{active}$. In some embodiments, the frequency of the body part's motion f is represented as a function of number of active frames, $$f = \frac{1}{(fr_{active}/C)/(\text{frame rate})}$$

In some embodiments, the activity level of the body part is calculated as a function of frequency f (in Hz) and duty cycle D (%). In some embodiments, cycle time is computed by monitoring the crossing of the moving ROI and the stationary gating region. In some embodiments, cycle time is computed by monitoring the relative movement of the ROI and the stationary gating region. In some embodiments, the two positive-to-negative, or negative-to-positive, crossings identify the periodic properties. In some embodiments, a period is defined as the time lapse between every pair of positive to negative zero crossings. In some embodiments, the mean value of these estimated periods were taken as the cycle time. In some embodiments, the device calculates the duty cycle, D as the percent of time over the observation duration when at least one of the velocity of the ROI or the acceleration of the ROI is greater than a threshold. In some embodiments, the processor of the devise is further configured to perform the following steps: use a past trajectory history; incorporate a suitable statistical state transition model; predict a new ROI position; use the predicted new position as a ground truth for the next tracking cycle; and update and correct a state model by the new location every iteration in order to maintain the accuracy of the prediction.

In some embodiments provided herein is a system for measuring spatiotemporal characteristics of repetitive motion activities, comprising: a) an image capture component; b) an input component that receives a selection of a single, or multiple, region, or regions, of interest (ROI) on an image of a body; c) a processor component for identifying and tracking motion of the ROI without any sensors or other motion capture instrumentation being applied to the body, further comprising a component for performing cyclic motion analysis on the ROI, and a component for quantifying spatiotemporal characteristics of the ROI; and d) an output component for the user to receive information about the repetitive motion activities of the ROI. In some embodiments, the system has a component that provides feedback to permit a user to prevent repetitive motion injuries. In some embodiments the image capture component communicates directly with the processor in real-time. In some embodiments, the image capture component records and stores the video footage to be later processed by the processor. In some embodiments, a single video camera captures the image. In some embodiments, multiple video cameras capture the image. In some embodiments the camera distance is fixed and is used to calibrate velocity and acceleration. In some embodiments the distance from the observed body part to the camera is variable, and is measured using an optical or video continuous distance-measuring component. In some embodiments, the input component is further configured to receive a selection of a stationary region (ROS) in the image background. In some embodiments, the input component is an interactive interface between the system and the user. In some embodiments the user interface is a computer or monitor. In some embodiments the user interface is a portable computer. In some embodiments an algorithm identifies the ROI. In some embodiments an algorithm identifies the ROS. In some embodiments, the processor is configured with a marker-less algorithm that uses video from a single standard camera to track motion with sufficient accuracy to evaluate injury risk to a body or a subject under field conditions. In some embodiments, the processor is configured to quantify repetitive motion of a video region of interest (ROI) that has been selected by a user from an image of a part of a body. In some embodiments, the processor component is further configured to perform a cyclic motion analysis using an algorithm that calculates the frequency and duty cycle of the ROI. In some embodiments, the processor component is further configured to quantify spatiotemporal characteristics of the ROI using an algorithm that calculates values including, but not limited to, the velocity and acceleration of the ROI. In some embodiments, the processor component is further configured to calculate a quantitative activity level as a function of the cycle time and the duty cycle. In some embodiments, the system further comprises: a calculation of an activity level of the ROI using a cross-correlation based tracking algorithm that is initialized by selecting a polygonal ROI in order to identify the focal area; a template matching tracking algorithm that tracks the ROI motion trajectory over successive video frames; a cyclic motion analysis algorithm that estimates the cycle time based on boundary-crossings of the ROI relative to the ROS; an estimation of duty cycle as the fraction of cycle time that a moving speed of the ROI was greater than a threshold; and an estimation of the activity level calculated as a function of the cycle time and the duty cycle. In some embodiments one or more polygonal region(s) are selected. In some embodiments said algorithm further facilitates a method comprising: obtaining a motion history curve with positive and negative values from motion tracking; determining frame numbers that contain the boundary-crossing; defining a cycle as the period of time between two positive-to-negative or two negative-to-positive boundary-crossing points; and performing the boundary-crossing detection on a filtered curve. In some embodiments the image capture device is a video camera that communicates with the processor. In some embodiments the processor is within a computer. In some embodiments the user interface is a computer or monitor. In some embodiments the processing takes place in real-time. In some embodiments the processing takes place with a time delay or at a remote location. In some embodiments, the output received by the user includes quantification of the activity level of the ROI. In some embodiments, the output received by the user includes quantification of, and analysis about, the spatiotemporal characteristics of the ROI. In some embodiments the system has a component that generates a report designed to prevent repetitive motion injuries. In some embodiments, the output component generates a descriptive information product based on the calculated activity level and the spatiotemporal information of the ROI. In some embodiments, the descriptive information product contains a warning of possible dangers associated with the calculated activity level and the spatiotemporal information of the ROI. In some embodiments the system is contained within a single unit that is small enough to be carried comfortably and used by an individual. In some embodiments said unit weighs less than or equal to six kilograms. In some embodiments the system is embodied in a hand-held computer. In some embodiments said hand-held computer is camera-enabled. In some embodiments the system resides within a smart cellular phone. In some embodiments the system is embodied in a computer with a touch-screen. In some embodiments the system is embodied within a computer with an interactive visual display. In some embodiments the system further comprises a mounting component used for installation it is used at the location where a subject usually incurs repetitive motion. In some embodiments said location is an occupational setting. In some embodiments the location is an industrial setting. In some embodiments the location is a workplace. In some embodiments the system further comprises a component that provides feedback to permit a user to prevent repetitive motion injuries. In some embodiments, the system is configured to determine which occupational activities are likely to cause injuries. In some embodiments, the system is configured to determine which occupational activities are likely to cause muscle fatigue. In some embodiments, the output component generates a descriptive information product based on the calculated activity level and the spatiotemporal information of the ROI. In some embodiments, descriptive information product contains a warning of possible dangers associated with the calculated activity level and the spatiotemporal information of the ROI.

In some embodiments provided herein is a method comprising the following steps: a) directing an image-capture device to record visual information from at least one body part of a subject that is engaged in a repetitive motion; b) using an interface component, or an automated vision-based algorithm, to select at least one video region of interest (ROI) on said body part, or parts, and to select a stationary video region (ROS) in the image background; and c) receiving a report generated by a processor component. In some embodiments, the report provides an estimate of the activity level of the ROI. In some embodiments, the report provides an estimate of possible repetitive motion dangers associated with the calculated activity level and the spatiotemporal information of the ROI. In some embodiments, the method further comprises using the processor component to identify motion of the video ROI without the use or application of any markers on said subject. In some embodiments, the method further comprises using the processor component to track motion of the video ROI. In some embodiments, the method further comprises using the processor to measure spatiotemporal characteristics of the selected ROI in a video field, such as, but not limited to, movement velocity and acceleration. In some embodiments, the method further comprises using the processor to quantify a frequency and a duty cycle of the selected ROI. In some embodiments, the method further comprises using the processor to calculate an activity level estimate of the ROI, wherein the activity level is estimated as a function of the cycle time and the duty cycle. In some embodiments, the method further comprises using the processor to quantify and analyze the spatiotemporal characteristics of the ROI. In some embodiments, the method further comprises selecting the subject to perform the repetitive motion activity. In some embodiments, the method further comprises selecting the repetitive motion to be performed. In some embodiments, the method further comprises selecting which body part, or parts, to be observed. In some embodiments, the method further comprises using the interface to select a stationary background region (ROS). In some embodiments the motion tracking is marker-less and does not require use of any markers or external sensors other than the image capture component. In some embodiments, the processor component is configured to perform steps comprising: track motion of the video ROI without the use or application of any markers on said subject; quantify a frequency and a duty cycle of the selected ROI; calculate an activity level of the ROI; and quantify and analyze the spatiotemporal characteristics of the ROI. In some embodiments the processor component performs the tracking, measuring, quantifying and reporting steps automatically in real-time. In some embodiments the ROI is on an image of a part of a body, and the method provides a measure of an activity level of the body part. In some embodiments visual information may be recorded from multiple body parts. In some embodiments multiple ROI(s) are on images of multiple body parts, and the method provides a measure of activity level for each of those body parts. In some embodiments, the method is accomplished using separate components. In some embodiments, the method is accomplished using a system that comprises an image-capture device, a processor device, and a user interface device that provides for user input and provides output to the user. In some embodiments, the method is accomplished using a single repetitive motion assessment device. In some embodiments, the method is accomplished using a single device that comprises an image-capture component, a processor component, and a user interface component. In some embodiments, the device is direct video assessment device. In some embodiments, the processor component is configured to use an automated vision-based method to estimate the motion of the image-capture component. In some embodiments, the image-capture component is a camera. In some embodiments, the processor is configured to compensate for motion of the image-capture component to produce a more accurate estimate of the activity level of the ROI. In some embodiments, the image-capture component further comprises: an attached motion detector, such as, but not limited to, a gyroscope or an accelerometer. In some embodiments, the processor is further configured to estimate the motion of the device by extracting and processing the reading from the attached motion detector, and using the motion estimate to provide a better estimate of the activity level of the ROI. In some embodiments, the method further comprises using the processor component to calculate loading of the ROI, based on spatiotemporal characteristics of the ROI, such as, but not limited to, a time during which the ROI is loaded. In some embodiments, the processor is further configured to perform steps comprising: a) initializing an algorithm to track a single region, or multiple regions, of interest (ROI) in order to identify one or more focal area(s) of an object; b) using an automated vision algorithm to track the ROI's motion trajectory over successive video frames; c) using an automated cyclic motion analysis algorithm to estimate a cycle time based on the ROI's motion; d) estimating the duty cycle of the ROI as a fraction of the cycle time that specific spatiotemporal characteristics of the ROI are satisfied; and e) automatically estimating the activity level of the ROI by calculating said activity level as a function of the cycle time and the duty cycle. In some embodiments, the processor is further configured to record a motion history curve for each region of interest. In some embodiments, the processor is further configured to use the recorded motion history curve as part of its cyclic motion analysis of the ROI. In some embodiments the processor is further configured to do the following steps, comprising: calculating an activity level of the ROI using a cross-correlation based tracking algorithm that is initialized by selecting a polygonal region of interest (ROI) in order to identify the focal area; tracking the ROI motion trajectory over successive video frames, using a template matching tracking algorithm; and estimating the cycle time based on boundary crossings of the ROI relative to a stationary gating region, using a cyclic motion analysis algorithm, wherein a duty cycle is estimated as the fraction of cycle time that a moving speed of the ROI was greater than a threshold, and wherein an activity level estimate, in turn, is calculated as a function of the cycle time and the duty cycle. In some embodiments the ROI is on an image of an arm or a hand of a human body, and the method provides a measure of the hand activity level (HAL).

In some embodiments provided herein is a method comprising the steps of: initializing a cross-correlation based tracking algorithm after a user selects a region of interest (ROI) in order to identify a focal area of an object; tracking the ROI motion trajectory over successive video frames, using a template matching tracking algorithm; estimating a cycle time based on crossings of the ROI relative to a stationary background region, using a cyclic motion analysis algorithm; estimating duty cycle as a fraction of cycle time that a moving speed of the ROI greater than a threshold; and estimating an activity level by calculating the activity level as a function of the cycle time and the duty cycle. In some embodiments, multiple ROIs are selected. In some embodiments, one or more polygonal ROI(s) are selected. In some embodiments said method further comprises: obtaining a motion history curve with positive and negative values from motion tracking; determining frame numbers that contain the boundary-crossing; defining a cycle as the period of time between two positive-to-negative or two negative-to-positive boundary-crossing points; and performing the boundary-crossing detection on the motion history curve, or on a smoothed motion history curve. In some embodiments the method further comprises: using a processor configured to conduct the analytic and quantitative components of the method; using an image capture device to collect the data; and using a user interface that interacts with the processor.

FIGURE DESCRIPTION

In the detailed description of embodiments of the invention presented below, reference is made to the accompanying drawings in which:

FIG. 8 is an exemplary embodiment of a repetitive motion analysis system implemented as a hand-held camera enabled device. This illustrates an analyst (the user) aiming the device at a seated operator performing a repetitive task. The analyst inputs via a touch screen the location in the camera field that is designated the stationary region (ROS in diagram) and region of interest (ROI), which is one of the operator's hands. The diagram also indicates:
- A. A human subject performing repetitive motion task at a seated workstation.
- B. The stationary corner of the workstation.
- C. A human analyst (the user) using the touch screen interface to indicate the ROI and ROS and input other commands.
- D. The touch screen input interface.
- E. The camera lens of the device.
- F. The video monitor and the touchscreen.
- G. The output display of Frequency, Duty Cycle and HAL.

DETAILED DESCRIPTION OF THE INVENTION

Provided herein are devices, systems and methods that use video analysis to measure repetitive motion activity of a designated body part, including velocity, acceleration, frequency, and duty cycle, without applying sensors or other instrumentation to the body, for the purpose of preventing repetitive motion injuries.

While one embodiment envisions the main subject of this method and system being human employees working in an occupational setting, this method and system may be applied to other subjects. While one embodiment envisions this method and system to be used to measure the Hand Activity Level (HAL), Latko et al., supra, other forms of repetitive motion activity may be measured. The sensor that collects the visual information may be any sort of imaging component capable of light information about the physical movement and recording it as a series of sequential images. A processor that analyzes the data may be contained within the sensor device or separate from the sensor device. One embodiment envisions a compact device containing the sensor, the processor, and an interface by which a user may directly review the results. Other embodiments allow the interface to be separate from the other components, so long as the processor is capable of communicating to the interface. In some embodiments, a person or business uses the device or method or system to measure repetitive motion activity of an employee to prevent muscle fatigue or a repetitive motion injury, or for rehabilitation or to prevent re-injury after occurrence of an initial injury. Appropriately used, the device and methods and systems provide significant value in preventing muscle fatigue or repetitive motion injuries such as sprains, strains, tendinitis, tendosynovitis, carpal tunnel syndrome, or other repetitive motion injury.

Subject.

While one embodiment envisions the main subject of this method and system or device being human employees working in an occupational setting, this method and system may be applied to other subjects. Said subject may be involved in non-occupational work, in hobbies, in acts of daily living, or in other activities. In some embodiments, the main subject may be an animal engaged in repetitive motion activities, such as a horse, for example. In some embodiments, the main subject may be mechanical, such as a robot or a robot arm or other mechanical device or component.

Motion being Measured.

While one embodiment envisions this method and system or device to be used to measure the Hand Activity Level (HAL), the methods and systems or devices may be used to measure other activities. Any other forms of repetitive motion activity may be measured. Thus, while in one embodiment the system may measure upper extremity repetitive motion, such as of the hand or arm; in some embodiments it may measure lower extremity repetitive motion, such as of the foot, ankle leg or knee; in some embodiments it may measure repetitive motion of the head, neck or trunk.

Sensor.

The sensor that collects the visual information may be any sort of imaging component capable of light information about the physical movement and recording it as a series of sequential images. Said sensor may be any type of video camera capable of communicating with a processor, including but not limited to, a professional video camera, a camcorder, a pan tilt zoom camera, a webcam, a digital video recorder, a digital camera, a mobile phone, a smart phone, or a camera on a computer.

Processor.

Figure 1:
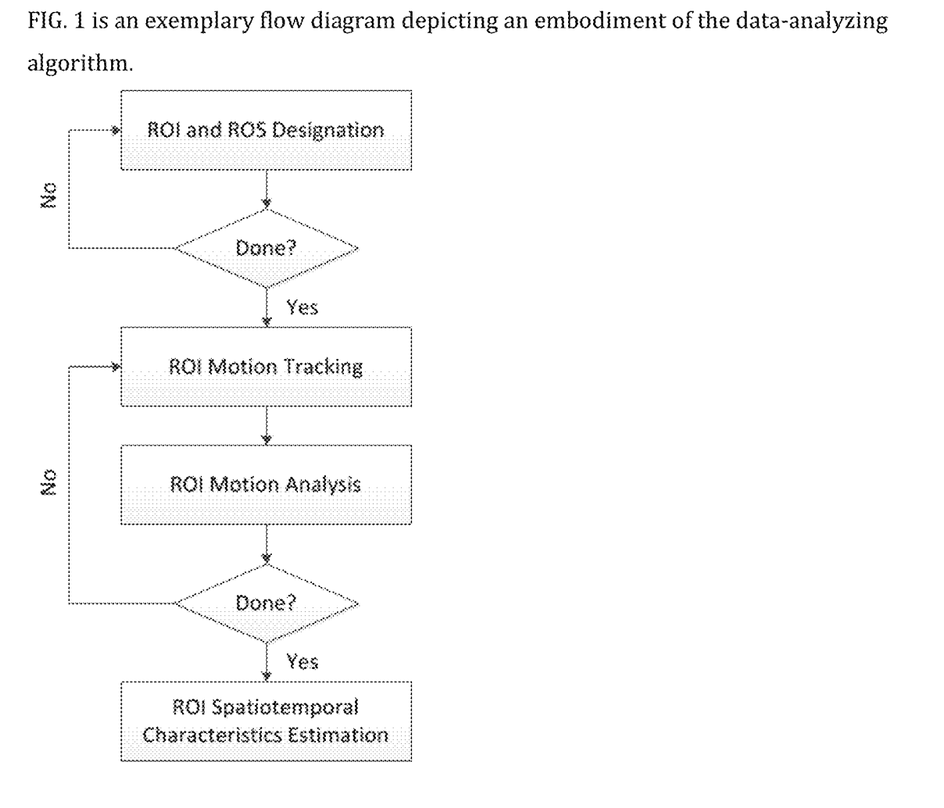
FIG. 1 is an exemplary flow diagram depicting an embodiment of the data-analyzing algorithm.
Figure 2:
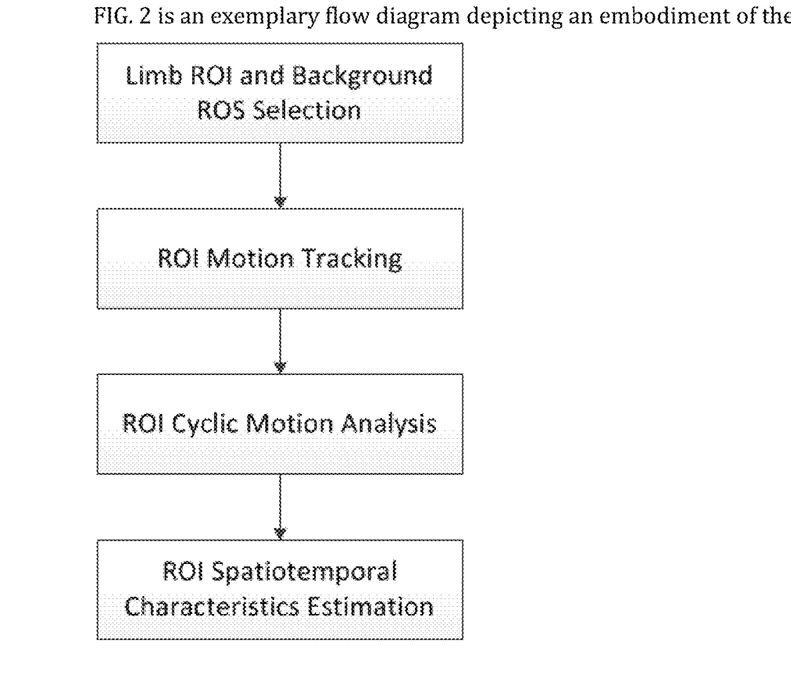
FIG. 2 is an exemplary flow diagram depicting an embodiment of the algorithm.
Figure 3:
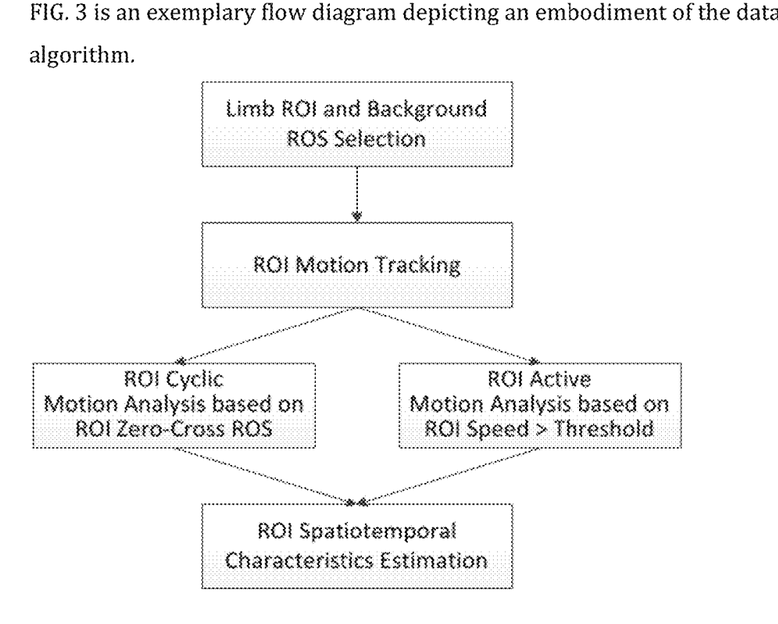
FIG. 3 is an exemplary flow diagram depicting an embodiment of the data-analyzing algorithm.
Figure 4:
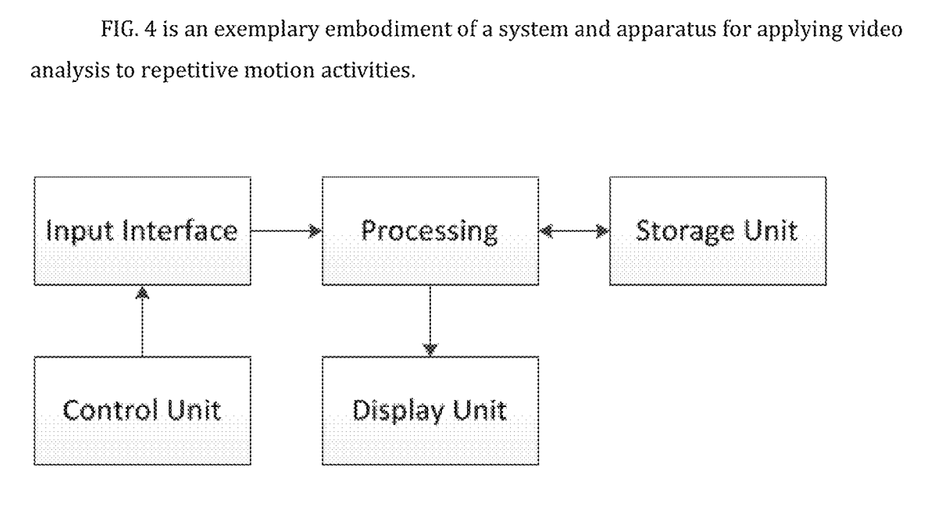
FIG. 4 is an exemplary embodiment of a system and apparatus for applying video analysis to repetitive motion activities.
Figure 5:
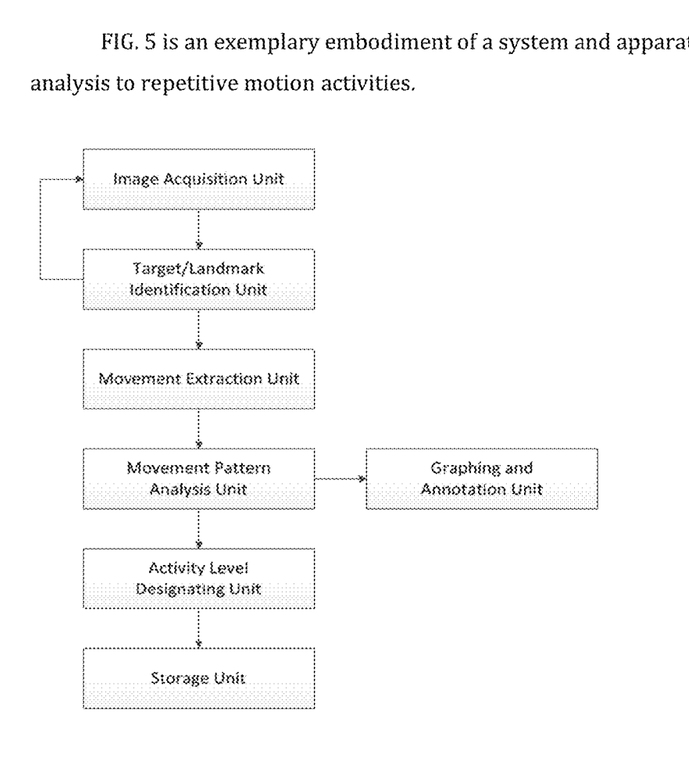
FIG. 5 is an exemplary embodiment of a system and apparatus for applying video analysis to repetitive motion activities.
Figure 6:
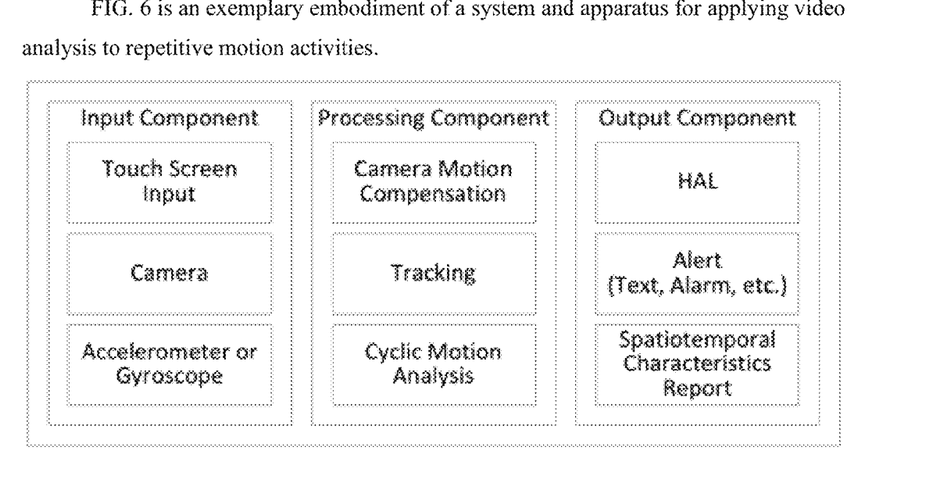
FIG. 6 is an exemplary embodiment of a system and apparatus for applying video analysis to repetitive motion activities.
Figure 7:
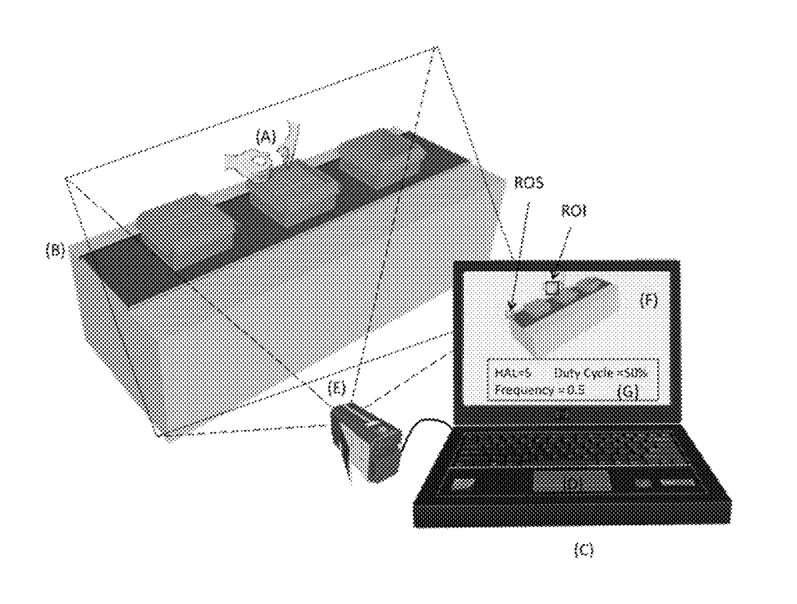
FIG. 7 is an exemplary embodiment of a repetitive motion analysis system implemented as a separate video camera and software executed on a laptop computer. This illustrates a camera aimed at a seated operator performing a repetitive task. The analyst uses the computer mouse to input the location in the camera field that is designated the stationary region (ROS in diagram) and region of interest (ROI), which is one of the operator's hands. The diagram also indicates:
- A. A human subject performing a repetitive motion task at a seated workstation.
- B. The stationary corner of the workstation.
- C. A laptop computer executing the software.
- D. The laptop input interface used to indicate the ROI and ROS and input other commands.
- E. The video camera used to record the repetitive motion activity.
- F. The laptop computer screen displaying the video and program output.
- G. The output display of Frequency, Duty Cycle and HAL.
Figure 8:
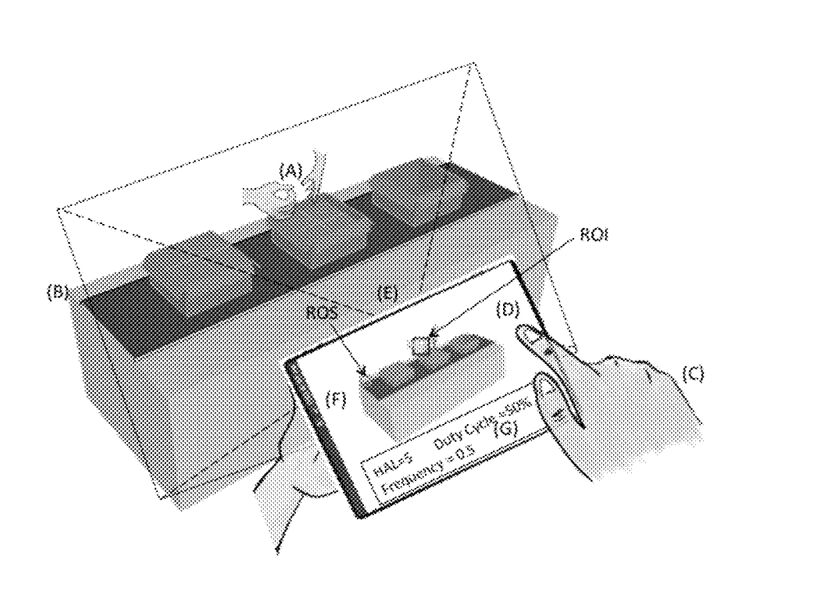

The processor that analyzes the data may be contained within the sensor device or separate from the sensor device. If the processor is a computer processor, it may be part of the device containing the sensor, such as a digital camera, smart phone, computer or other camera-enabled hand-held device; or it may receive information communicated from the sensor. The processor may be within a portable computer such as a personal digital assistant, a hand-held organizer, a palm-top computer, a pad or tablet computer, or a lap-top computer, or some other portable computer; or it may be within a larger, non-portable device such as a desk-top computer. The processing may take place live, in real-time, or after the fact. The processing may occur at the location where the sensing occurs or at a remote data processing center. Exemplary data collection, analysis, and reporting methods employing such processors are shown in FIGS. 1 through 8 and the Examples section below.

Interface.

One embodiment envisions a compact device containing the sensor, the processor, and an interface by which a user may directly input information, view and interact with overlaid images on a video display and review the results, such as a touch screen. Other embodiments allow the interface to be separate from the other components, so long as the processor is capable of communicating to the interface. The interface may indicate the results by any of a number of means, including but not limited to such visual or audio means as raw data, numerical data, graphical representation, pictorial representation, description through words, or representation through audio frequencies. The interface may be on a portable device such as a personal digital assistant, a hand-held organizer, a palm-top computer, a pad or tablet computer, a touch screen computer, or a lap-top computer, or some other portable computer; or it may be on a larger, non-portable device such as a desk-top computer, a monitor or a television. This list is intended by way of example, but not to limit the possible venues for the interface. Other embodiments allow the interface to communicate directly to a computer that has been programmed to respond to the results of this method or system.

User.

While one embodiment envisions the main user of this method and system or device being a trained human analyst in an occupational setting, other users may also use this method and system or device. Said user may be a supervisor, employee, family member or friend of the subject. Said user may be a health-care worker. Said user may be a person whose only training in use of the method and system or device comes from instructions accompanying the system or device or incorporated within the user interface of the of the system or device. Said user may be a non-human artificial intelligence capable of operating the system or device, such as a robot or robot arm equipped with visual sensors. In some embodiments, a person or business uses the methods and systems or devices to measure repetitive motion activity of an employee to prevent repetitive motion injury, to evaluate and compare different jobs or changes in job design, or to prevent re-injury after occurrence of an initial injury. Appropriately used, this method and system or device provides significant value to employers in preventing employees from incurring work-related repetitive motion injuries such as sprains, strains, tendinitis, tendosynovitis, and carpal tunnel syndrome. It finds use for individuals engaged in repetitive motion tasks in order to adapt their motion parameters and prevent injury (e.g., athletes). Additionally, in some embodiments it is used by a healthcare worker as a tool in predicting the possibility of repetitive motion injury or in proposing appropriate therapy. In some embodiments, it finds use to track activity of a subject, or to provide data to improve performance. In some embodiments, devices in parallel using the methods and systems find use to measure and report on activity of a system of operations. However, it should not be construed as being limited to those purposes.

Examples

The following examples are provided to illustrate certain non-limiting embodiments of the technology.

Experimental Example

Digital video processing is used to automatically measure repetitive motion exposure. A direct video assessment method has several advantages over commonly used observational and instrumentation methods. It is objective, can automatically perform the analysis in real-time, requires minimum human intervention, and is determinate for a given video segment. The noninvasive real-time video content analysis framework automatically measures limb activity levels using conventional digital videos focused on the work activity. This has several advantages over traditional methods. First, it is automatic and can perform the analysis in real-time. Second, it employs only minimum human intervention and discretion. Consequently the subjectivity issue is eliminated since the analysis is determinate for a given video segment. Third, in some embodiments, such a system is ported to programmable, camera-enabled mobile devices. This lowers the instrumentation barrier and makes analysis of repetitive motion occupational hazards more accessible to general industry.

In some embodiments, the system analyzes digital video, either recorded or from a real-time video stream. The video is processed and analyzed, and an estimate of the limb's activity level is generated. Since two important parameters for quantifying the limb's activity level are the period of repetitiveness and the duty cycle of the limb's activities, a region of interest is observed for changes over a period of time. The pixel intensity representing a sub-image is recorded and stored in an intensity history with respect to time (frame number), to facilitate later analysis. In some embodiments, the content analysis portion of the framework is comprised of two components, motion-tracking and cyclic motion analysis.

In some embodiments, the motion-tracking component performs body part tracking in real time. An algorithm identifies and reports the new location of the region under investigation as the video stream advances in time. This localization information is further processed in order to assess the speed and direction of the movement between two or more video frames.

The cyclic motion analysis component determines what movements constitute a cycle. After the cyclic pattern is identified, the system divides the analyzed sequence into repetitive cycles. Parameters such as frequency and duty cycle of the movements can therefore be determined through using the recorded speed/direction history. These parameter values are used to quantify the body part's activity level.

Several exemplary tracking methods are described herein to illustrate principles of the technology. Normalized cross correlation template matching is commonly employed for motion tracking and motion estimation. The goal of template matching is to find out the new center location $(x_i, y_i)$ of the template in frame i within the search range, which gives the largest similarity score. A similarity score is determined by various evaluation functions. One of the simplest forms is the sum of squared difference. Alternatively, optical flow may be used to represent the apparent motion of brightness patterns in an image. In one embodiment, the feature point is extracted within a fixed image patch using a strong corner extraction method, with these feature points tracked using a pyramidal Lucas-Lanade feature tracker. JEAN-YVES BOUGUET, OPENCV DOCUMENT, INTEL CORPORATION, MICROPROCESSOR RESEARCH LABS, PYRAMIDAL IMPLEMENTATION OF THE LUCAS-KANADE FEATURE TRACKER (2000), available at robots.stanford.edu/cs223b04/algo_tracking.pdf.

The video content analysis algorithm is able to recognize and identify the pattern of repetitive motion, through a process known as cyclic motion analysis. Determination of the cycle pattern provides essential parameters for determining a body part's activity level, and thereby allows determination of the body part's activity level.

In some embodiments, a motion history curve with positive and negative values is obtained from motion tracking. To define a cycle, the frame numbers that contain the boundary-crossing are determined. A cycle is then defined as the period of time between two positive-to-negative (or two negative-to-positive) boundary-crossing points. Since the original motion history curve may be noisy, the boundary-crossing detection is performed on a filtered curve, such as the high frequency removed direction curve.

In some embodiments, the method used to identify cycles is by detection of crossings of a gating patch. For example, a current block location may be centered at $(x_c, y_c)$, and the gating patch location centered at $(x_g, y_g)$. The two coordinates are compared, and the relative horizontal positions of the current block and the reference gating block are determined, e.g., whether the current block is on the right of the gating block $(x_c > x_g)$, or the current block is on the left of the gating block $(x_c \leq x_g)$. A cycle is defined as the period of time between two right-to-left (or left-to-right) gating patch crossings. The crossing points, or frame numbers are recorded as list $fr = \{fr_0, fr_1, fr_2, \ldots\}$.

In some embodiments, the processor is further configured to run a cross-correlation based template-matching algorithm to track a motion trajectory of a selected region of interest (ROI) over successive video frames for a single camera to measure repetition frequency, duty cycle and activity level. In some embodiments, a user initializes a cross-correlation based tracking algorithm by selecting an ROI in order to identify the focal area such as a spot on the hand or arm; and the tracking algorithm tracks the ROI motion trajectory over successive video frames. In some embodiments, the ROIs are polygonal. In one embodiment, the ROI is a rectangular region on the upper limb. In one embodiment, the focal area may be the hand or arm, resulting in measurements of the hand activity level (HAL). In some embodiments, the template matching tracking algorithm tracks the ROI motion trajectory over successive video frames. In some embodiments, the user designates a stationary gating region (ROS). In some embodiments, the cyclic motion analysis algorithm estimates cycle time based on boundary-crossings of the ROI relative to the ROS.

To some embodiments, denote $r_i$ to be a vector of intensity values of all pixels within the ROI at the $i^{th}$ frame, and $r_{i+1}(w)$ to be a candidate ROI at the $(i+1)^{th}$ frame with a displacement of $w \in \Omega$ in a pre-specified search area. $\Omega$ is determined based on the prior knowledge of the speed of arm movement (pixels/frame). In some embodiments, the cross-correlation between $r_i$ and $r_i+1(w)$ is defined as the angle between these two vectors ($\|r_i\|$ is the magnitude of the vector $r_i$, $r_i^T$ is the transpose of $r_i$):

$$R(w) = r_i^T r_{i+1}(w) / (\|r_i\| \cdot \|r_{i+1}(w)\|)$$

In some embodiments, the displacement $w^* = \arg\max_w R(w)$ determines the updated position of the ROI at the $(i+1)^{th}$ frame, $r_{i+1} = r_{i+1}(w^*)$. The sequence of $w^*$ is recorded as the velocity of the motion between these two frames, and the new position of the ROI yields the motion trajectory at the $(i+1)^{th}$ frame.

In some embodiments, cycle time may be computed by monitoring the crossing of the moving ROI and the stationary gating region. In some embodiments, a cycle is defined as the time elapsed between consecutive gating region crossings from the same direction. In some embodiments the motion tracking provides positive and negative values. In one embodiment, the two positive-to-negative (or negative-to-positive) crossing identify periodic properties of the moving ROI. In one embodiment, a period is defined as the time lapse between every pair of positive to negative zero crossings. In one embodiment, cycle time is defined as the mean value of the estimated periods.

In some embodiments, the processor is further configured to compute a motion history curve with positive and negative values obtained from motion tracking, wherein the frame numbers that contain the boundary-crossing are determined, and wherein a cycle is defined as the period of time between two positive-to-negative, or two negative-to-positive, boundary-crossing points.

In some embodiments, the recorded pixel data location values are passed through a filter. In one embodiment, the recorded video data pixel location values are low-pass filtered. In some embodiments, the boundary-crossing detection is performed on a filtered curve. In one embodiment, the boundary-crossing detection is performed on a high frequency removed direction curve. In some embodiments the algorithm identifies cycles by detecting crossings of a gating patch, and a cycle is defined as the period of time between two right-to-left, or left-to-right, gating patch crossings. In some embodiments a cyclic motion analysis algorithm estimates the cycle time based on boundary-crossings of the ROI relative to a stationary gating region.

In some embodiments, the processor is further configured to calculate a velocity $(v_x, v_y)$ vector and an acceleration $(a_x, a_y)$ vector for the center of the ROI at each time stamp as follows:

$$v_{p,i}=(p_{i+1}-p_{i-1})/2\Delta$$

$$a_{p,i}=(p_{i+1}-2\times p_i+p_{i-1})/\Delta^2$$

wherein $p\in\{x,y\}$, $i\in\{2, 3, \ldots\}$ and $\Delta=\frac{1}{30}$ second, which is the sample rate of the video. The video velocity and acceleration magnitude are determined by:

$$v_{xy,video}=\sqrt{(v_x)^2+(v_y)^2}$$

$$a_{xy,video}=\sqrt{(a_x)^2+(a_y)^2}$$

In some embodiments the processor is further configured to compute duty cycle D as the fraction of cycle time that the ROI's moving velocity was greater than a threshold; and to compute activity level of the body part as a function of the cycle time and the duty cycle. In some embodiments, the HAL estimate, in turn, is calculated as a function of the cycle time (frequency in Hz) and the duty cycle (%).

In some embodiments, given a list of P frame numbers $fr=\{fr_0, fr_1, fr_2, \ldots, fr_{P-1}\}$ in which crossing occurred, the number of cycles C is defined as:

$$C=(\# \text{ of elements in } fr)-1=P-1$$

In some embodiments, the duty cycle D is defined as the ratio of exertion time with respect to total cycle time, or equivalently, the ratio of number of exertion frames to the total number of frames. The number of exertion frames is denoted as $fr_{exert}$, and the total number of frames within the entire observation is denoted as $fr_{total}$. Duty cycle D is determined by:

$$D=(fr_{exert}/fr_{total})\times 100\%.$$

In some embodiments, the frequency of the body part's motion f is determined by the time the body part is moving, as if the task is done at 100% duty cycle. Therefore frequency f is defined as inverse of average active cycle time. The active cycle time is measured in turns of number of active frames, where active frames are defined as those frames that have motion speed larger than or equal to a predefined threshold. The number of active frames is denoted as $fr_{active}$. The frequency of the body part's motion f is represented as a function of number of active frames:

$$f = \frac{1}{(fr_{active}/C)/(\text{frame rate})}$$

In some embodiments, the hand activity level HAL is calculated as a function of frequency f (in Hz) and duty cycle D (%).

In some embodiments, to address problems of occlusion and disappearance, the tracking system makes use of the past trajectory history. By incorporating a suitable statistical state transition model, it predicts the new ROI position. This predicted new position is used as the ground truth for the next tracking cycle. The state model is updated and corrected by the new location at each iteration in order to maintain the accuracy of the prediction.

In some embodiments, the processor compensates for camera motion by tracking background patches or strong corner points, in addition to tracking the ROI. The motion of these patches or corners are averaged together and provide an estimate of the camera motion. In some embodiments, the processor estimates camera motion by receiving input from a device such as a gyroscope or accelerometer attached to the camera to provide the orientation and motion information of the camera. In some embodiments, the estimated camera motion information is used to correct the hand displacement quantity and provide better a more accurate estimate of the HAL.

The video-based direct exposure assessment method has significant advantages. The use of marker-less video is unobtrusive and does not interfere with the job and possibly movement patterns and exertions. The marker-less video approach is made practical by relaxing the need for high precision, which is not necessary for limb activity levels, and by adopting a semi-automatic approach whereby the analysts interactively selects a region of interest such as a hand or arm to track relative to a stationary region, rather than imposing an a priori model of the tracked activity. Consequently the analysis complexity is greatly reduced and may be more tolerable of the numerous variations encountered in field video recordings of occupational tasks. Furthermore such an application may be ported to programmable, camera-enabled mobile devices. It is contemplated that this lowers the instrumentation barrier and makes analysis of upper limb work-related occupational hazards more accessible to general industry. The reduced instrumentation cost allows broader study, and may help reduce the risk of repetitive motion injuries in the work place.

What is claimed is:

1. A device comprising:
an input component configured to select a single or multiple regions of interest from an image of a subject's hands or arms or a background of the image of the subject's hands or arms, or a stationary region from a background;
a processor component configured to identify and track spatiotemporal characteristics of at least one region of interest (ROI) on an image of the subject's hands or arms without application of sensors or other instrumentation to the subject's body,
wherein the processor, in operation, is configured to:
identify motion of the ROI;
perform cyclic motion analysis on the ROI;
quantify kinematic properties of the ROI, said kinematic properties comprising velocity, acceleration, and spatiotemporal characteristics;
ascertain a duty cycle of the subject's forceful hand exertions from threshold level crossings of the kinematic properties of the ROI and repetition frequency of a task being performed by the subject; and
an output component configured to provide information from the processor about the repetitive motion and hand exertions of the subject comprising repetition frequency, duty cycle, and hand activity level (HAL) of the subject for preventing injuries due to repetitive motion or muscle fatigue.

2. The device of claim 1, wherein the device further comprises an image capture component selected from the group consisting of a camera and a video recorder, that is configured to communicate with the processor.

3. The device of claim 2, wherein the image capture component is a camera; and wherein the device further comprises: a camera motion compensation component selected from the group consisting of a gyroscope or an accelerometer, wherein the camera motion compensation component provides an estimate for the camera motion; and a processor component that is further configured to compensate for camera motion.

4. The device of claim 1, wherein the device further comprises: a recording component that records spatiotemporal characteristics representing a sub-image or video ROI; and a storage component that stores spatiotemporal characteristics in a history array, or journal, with respect to time.

5. The device of claim 1, wherein the assessment of temporal properties of cyclic movement to quantify repetitive motion and hand exertions of the subject is based on pixel-based spatiotemporal properties of a tracked ROI relative to a stationary landmark.

6. The device of claim 5, wherein the processor component is further configured to perform body part tracking in real time; wherein an algorithm identifies and reports a new location of the region under investigation as a video stream advances in time; and an algorithm processes the new location information to assess the spatiotemporal characteristics of movement between two or more image frames.

7. The device of claim 1, wherein the processor is configured to calculate the duty cycle of the subject's hand exertions based on the percentage of time that the hand is load bearing over cycle time.

8. The device of claim 1, wherein the measured region, or regions, of interest is, or are, on an arm or a hand of a human body, and the quantified measure provided is the hand activity level (HAL) or duty cycle of the subject's hand exertions.

9. The device of claim 1, wherein the output component further comprises: a component that provides feedback to permit a user to prevent repetitive motion injuries or muscle fatigue.

10. The device of claim 1, wherein the output component further comprises: a component that generates a report that contains one or more of: a graphic output of the ROI's activity level relative to load; a graphic output of the ROI's activity level relative to time; duty cycle of the subject's hand exertions, a graphic output of risk to the subject of incurring a repetitive motion injury, relative to load, based on the calculated hand activity level of the subject; a calculation of the risk to the subject of incurring repetitive motion injuries based on the calculated hand activity level of the subject, given a calculated or specified load; a warning signal if the activity level exceeds a threshold value beyond which repetitive motion injury or muscle fatigue is likely; a textual description of possible precautions to decrease the risk of repetitive motion injury; and a graphic display of possible precautions to decrease the risk of repetitive motion injury or muscle fatigue.

11. A system for measuring spatiotemporal characteristics of repetitive motion activities, comprising: an image capture component and a device of claim 1.

12. The system of claim 11, wherein the output component generates a descriptive information product based on the calculated hand activity level of the subject from the spatiotemporal information of the ROI, wherein said descriptive information product contains a warning of possible dangers associated with the calculated duty cycle of the subject's hand exertions, hand activity level, and the spatiotemporal information of the ROI.

13. A method comprising:
 a) directing an image-capture device of claim 1 to record visual information from hands or arms of a subject that is engaged in a repetitive motion;
 b) using an interface component, or an automated vision-based algorithm, to select at least one video region of interest (ROI) on said hands or arms and to select a stationary video region (ROS) in an image background;
 c) using a processor component to perform steps comprising:
  i) tracking motion of the video ROI without the use or application of any markers on said subject,
  ii) measuring movement velocity and acceleration of a selected ROI in a video field,
  iii) quantifying a frequency and a duty cycle of the selected subject's forceful exertions,
  iv) calculating a hand activity level estimate of the subject, wherein the hand activity level is estimated as a function of the cycle time and the duty cycle of the subject's forceful exertions, and
  v) analyzing the spatiotemporal characteristics of the ROI; and
 d) generating a report that provides an estimate of the hand activity level of the subject.

14. The method of claim 12, wherein the method further comprises using the processor component to estimate the motion of the image-capture component, and to compensate for motion of the device to provide a more accurate estimate of the hand activity level of the subject comprising using an automated vision-based method, or receiving additional motion data from a gyroscope or an accelerometer attached to the image capture component.

15. The method of claim 12, wherein the method further comprises using the processor component to calculate loading of the subject, based on spatiotemporal characteristics of the ROI to ascertain a time during which the body part is loaded.

16. The method of claim 12, wherein the method further comprises generating a report of possible repetitive motion dangers associated with the calculated repetition frequency of the task being performed by the subject, hand activity level, and the duty cycle of the subject's exertions.

* * * * *

UNITED STATES PATENT AND TRADEMARK OFFICE
CERTIFICATE OF CORRECTION

| | |
|---|---|
| PATENT NO. | : 9,566,004 B1 |
| APPLICATION NO. | : 13/681538 |
| DATED | : February 14, 2017 |
| INVENTOR(S) | : Robert G. Radwin et al. |

It is certified that error appears in the above-identified patent and that said Letters Patent is hereby corrected as shown below:

In the Claims

CLAIM 14 reads: "The method of claim 12, wherein the method further comprises using..."
CLAIM 15 reads: "The method of claim 12, wherein the method further comprises using..."
CLAIM 16 reads: "The method of claim 12, wherein the method further comprises generating..."

HOWEVER, THEY SHOULD READ:

CLAIM 14: "The method of claim 13, wherein the method further comprises using..."
CLAIM 15: "The method of claim 13, wherein the method further comprises using..."
CLAIM 16: "The method of claim 13, wherein the method further comprises generating..."

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*